(12) United States Patent
Grabarnick et al.

(10) Patent No.: US 7,078,465 B2
(45) Date of Patent: Jul. 18, 2006

(54) PROCESS TO BROMOMETHYLATE AROMATIC COMPOUNDS

(75) Inventors: Michael Grabarnick, Beer Sheva (IL); Yoel Sasson, Jerusalem (IL)

(73) Assignee: Makhteshim Chemical Works, Ltd., Beer Sheva (IL)

( * ) Notice: Subject to any disclaimer, the term of this patent is extended or adjusted under 35 U.S.C. 154(b) by 35 days.

(21) Appl. No.: 10/488,010

(22) PCT Filed: Aug. 29, 2001

(86) PCT No.: PCT/IL01/00814

§ 371 (c)(1),
(2), (4) Date: Jul. 27, 2004

(87) PCT Pub. No.: WO03/018518

PCT Pub. Date: Mar. 6, 2003

(65) Prior Publication Data

US 2004/0242799 A1    Dec. 2, 2004

(51) Int. Cl.
*C08F 112/08*   (2006.01)
*C07D 333/02*   (2006.01)

(52) U.S. Cl. .................. 525/333.4; 549/29; 570/199
(58) Field of Classification Search ............ 525/333.4; 549/29; 570/199
See application file for complete search history.

(56) References Cited

FOREIGN PATENT DOCUMENTS

CH    560736 A    4/1975

OTHER PUBLICATIONS

Stephen H. et al., J of The Chem. Society, Chem Society, London, GB, vol. 117, 1920, pp. 510-527, XP008003601.*
A. Roedig "Reaction of bis(bromomethyl)ether with aromatic compounds" Houben-Weyl (1995) V. 4, pp. 484-487.

George A Olah "Synthetic Methods and Reactions" Communications (Aug. 1974) pp. 560-561.
J. March "Advanced Organic Chemistry" John Wiley & Sons; New York (1992) p. 550.
Mikael Begtrup et al Equilibrium Control Bromomethylation: An Expedient Route to 2-Amino-3-(3-hydroxy-5-methylisoxazol-4-yl)propionic Acid (AMPA) Synthesis (Sep. 1993) pp. 861-863.
Nupur Garg et al "Redioselective Bromomethylation of 1,2-Dialkylbenzenes" Synlett pp. 310-312.
Ried, Grabosch "Kondensation cyclischer Bishalogenmethyl-Verbindungen mit nichtaromatischen Amines" Chemische Berichte, (1958) pp. 2485-2495.
Stephen H et al "The Introduction of the Chloromethyl Group into the Aromatic Nucleus" Journal of the Chemcial Society, Chemical Society, London, GB (1920) vol. 117, pp. 510-527.
Szendey, Munnes "Konstitution und Eigenschaften des Biphenylen-(4,4')-bis-'methyl-atropiniumbromids!, einer biquartaren Atropinverbindung" Chemische Berichte (1961) pp. 38-42.
V. Braun "Die Einwirkung flussigen Ammoniaks auf organische Halogenverbindungen" Chemische Berichte (1937) pp. 979-993.
Jin Zavada et al "A Facile Synthesis of Hexadis(bromomethyl)benzene from Mesitylene" Synthesis p. 1132.

* cited by examiner

*Primary Examiner*—Johann Richter
*Assistant Examiner*—Chukwuma Nwaonicha
(74) *Attorney, Agent, or Firm*—Browdy and Newark, PLLC

(57) ABSTRACT

The present invention provides a process for bromomethylation of organic compounds, wherein said process is a two stage process comprising of the following stages: a) reacting paraformaldehyde with hydrogen bromide and separating bis-bromomethyl ether (BBME) from the reaction mixture, and, b) reacting BBME obtained in stage (a) with an organic compound in the presence of a Lewis acid, to obtain the bromomethylated organic compound. Further provided by the present invention is a process for the preparation of 4,4'-bis-(diethylphosphonomethyl)-biphenyl (BPMB).

25 Claims, No Drawings

PROCESS TO BROMOMETHYLATE AROMATIC COMPOUNDS

FIELD OF THE INVENTION

The present invention relates to the field of organic chemistry, particularly to the field of bromomethylation reactions.

BACKGROUND OF THE INVENTION

Halomethylation reactions are well known reactions of aromatic compounds. The predominant halomethylation reactions are chloromethylation and bromomethylation. In recent years chloromethylating reagents have been recognized as highly hazardous reagents. For example bis-chloromethyl ether has been identified as a carcinogen which is ban in many countries in the world. Hence, bromomethylating reagents which have been recognized as less hazardous than the chloro-analogues thereof, offer an alternative halomethylating agent. Furthermore, bromomethylated compounds are more versatile as synthetic intermediates than the chloro-analogues. Olah et al (*Synthesis* (Communications) (1974), (8), 560–561) describes other halomethylating agents and the application thereof in the halomethylating of substituted aromatic compounds. The advantages of bromomethylating agents in terms of regioselectivity has been demonstrated, for example, by Zavada et al (*Synthesis* (short papers) (1994) vol. 11, 1132) and Garg et al (*Synlett* (1998) vol. 3, 310–312). The advantageous reactivity of bromomethylating reagents has been described in U.S. Pat. No. 4,559,392 to Raban and Begtrup et al (*Synthesis* (1993), 861). Nonetheless, bromomethylating reactions require temperatures ranging from 60° C. and higher, pressure exceedingly higher than atmospheric pressure and long reaction time. The conditions of the reaction increase (e.g. higher temperature, longer reaction time) with the decreasing reactivity of the substrate. Often the selectivity of the reaction is adversely effected by these factors and reaction conditions which may result in the formation of undesirable by-products which lower the yield and complicate the isolation process, which subsequently, have an adverse impact on the economical value of the process.

In view of the aforementioned there is a long felt need for a bromomethylating process which is less hazardous than the analogous chloromethylation and is conducted under moderate conditions, wherein said process is of economical value.

It is therefore an object of the present invention to provide a bromomethylating process which can be applied readily to a wide variety of substrates, including substrates of relatively low reactivity.

It is another object of the present invention to provide a bromomethylating process which requires relatively moderate conditions in terms of temperature, pressure and time.

A further object of the present invention is to provide a bromomethylating process for the preparation of bis-bromomethyl biphenyl.

It is yet another object of the present invention to provide a process which overcomes the disadvantages of the prior art.

Other objects of the invention will become apparent as the description proceeds.

SUMMARY OF THE INVENTION

The present invention provides a process for bromomethylation of organic compounds, wherein said process is a two stage process comprising of the following stages:

a) reacting paraformaldehyde with hydrogen bromide and separating bis-bromomethyl ether (BBME) from the reaction mixture, and, b) reacting BBME obtained in stage (a) with an organic compound selected from among a group comprising of substituted or non-substituted phenyl, biphenyl, styryl, naphthyl, pyridyl, thiophene, 5 and 6 member heterocycles, polystyrenes and divinylbenzene-styrene copolymers, in the presence of a Lewis acid selected from among a group comprising of zinc bromide, $SnBr_4$ and $AlBr_3$, to obtain the bromomethylated organic compound.

Further provided by the present invention is a process for the preparation of 4,4'-bis-(diethylphosphonomethyl)-biphenyl (BPMB) which comprises the aforementioned stages (a) and (b); (a) reacting paraformaldehyde with hydrogen bromide and separating bis-bromomethyl ether (BBME) from the reaction mixture, followed by; (b) a reaction of BBME obtained in stage (a) with biphenyl in the presence of an aqueous solution of zinc bromide, thus obtaining 4,4'-bis-(bromomethyl)-biphenyl (BBMB), and further reacting BBMB obtained from stage (b) with triethyl phosphite to obtain BPMB.

DETAILED DESCRIPTION OF A PREFERRED EMBODIMENT OF THE INVENTION

The following description is illustrative of embodiments of the invention. The following description is not to be construed as limiting, it being understood that the skilled person may carry out many obvious variations to the process.

Percentages noted throughout the application are by weight unless specifically noted differently.

According to an embodiment of the present invention a two stage bromomethylation process is carried out wherein in the first stage (a) paraformaldehyde is reacted with hydrogen bromide according to reaction (1), wherein n is an integer greater than 1:

$$(CH_2O)n + HBr \rightleftharpoons BrCH_2OCH_2Br + H_2O \qquad (1)$$

The HBr used can be in gas form or as an aqueous solution of HBr. Preferably, the HBr solution in the reaction is a saturated solution under the reaction conditions. Preferably, a mixture of aqueous HBr and HBr gas are applied in the reaction. The reaction medium is aqueous, wherein water can be added as pure water or as part of the aqueous HBr solution used in the reaction. The reaction is carried out for 0.5 to 1.5 hours at a temperature between −3° C. and 20° C., preferably about 0° C. The product BBME creates an organic phase which is separated from the reaction mixture after termination of the reaction. Separation can be effected by various separation techniques known in the art, as can be appreciated by the skilled artisan.

According to a preferred embodiment of the invention, stage (a) of the process is carried out as a semi-batch process wherein HBr gas is slowly infused into the reaction medium which contains paraformaldehyde and water and optionally, an aqueous solution of up to 65% HBr.

According to yet a further embodiment of the invention, stage (a) is carried out in a molar excess of HBr, preferably maintaining the reaction medium saturated with HBr.

According to an embodiment of the invention, in stage (b) of the present process, BBME obtained from stage (a) is reacted with an organic compound R' according to reaction (2)

$$BrCH_2OCH_2Br + 2R' + 2A' \longrightarrow 2R'CH_2Br + H_2O \quad (2)$$

wherein R' is selected from among a group comprising of substituted or non-substituted phenyl, biphenyl, styryl, naphthyl, pyridyl, thiophene, 5 and 6 member heterocycles, polystyrenes and divinylbenzene-styrene copolymers, and A' is a Lewis acid selected from among a group comprising of $ZnBr_2$, $SnBr_4$ and $AlBr_3$, preferably, zinc bromide. In the case where monobromomethylation is desired, the mole ratio between BBME and the organic compound is in the range of 1.05:2 to 1.4:2 and the mole ratio between the Lewis acid and organic compound R' is in the range of 1:2 to 1.5:1. The reaction can be carried out with or without a solvent. The aforementioned ratios are adjusted by a factor in accordance to the number of bromomethyl group which are introduced into the organic compound, e.g., for dibromomethylation the amount of bromonetylating agent is doubled as is the Lewis acid. According to a preferred embodiment of the invention, stage (b) is carried out in an organic solvent selected from among a group comprising of alkanes and brominated alkanes, preferably dibromomethane. Preferable solvents do not contain chlorine substituents in order to avoid the formation of undesirable chlorinated by-products.

According to a further embodiment of the invention, zinc bromide is used in stage (b) wherein the mole ratio between ZnBr and the organic compound R' is about 1:1, and ZnBr is in the form of a 78 w/w % aqueous solution of zinc bromide.

The reaction in stage (b) is conducted for 2 to 8 hours, preferably 5 hours, at a temperature between 20° C. and 40° C., preferably about 20° C. to 30° C. The reaction can be conducted with or without a solvent, preferably in an organic solvent selected from among a group comprising of alkanes and brominated alkanes, preferably dibromomethane.

Following the reaction in stage (b) the reaction mixture is separated to an organic phase and aqueous phase. The bromomethylated product is separated from the organic phase. Separation techniques depend on the nature of the product. Non-limitative examples of separation techniques include extraction, distillation and crystallization.

According to a particular embodiment of the invention, 4,4'-bis-(bromomethyl)-biphenyl (BBMB) is prepared by reacting biphenyl as R' in stage (b) as described in reaction (3).

(3)

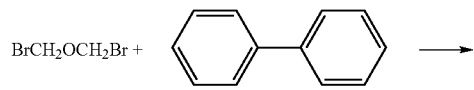

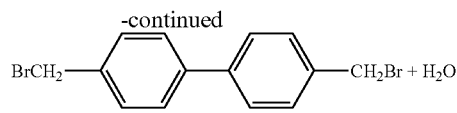

Accordingly, BBME obtained from stage (a) is reacted with biphenyl in the prsence of an aqueous 78% w/w solution of zinc bromide wherein the mole ratio between the zinc bromide and biphenyl is in the range of 1:1 to 3:1. The reaction is carried out in dibromomethane at a temperature in the range of about 20° C. to 40° C. for about 5 hours. The reaction mixture is then separated to aqueous and organic phases. The organic phase is treated such that BBMB is crystallized and recovered from the organic phase.

According to yet a further particular embodiment of the present invention, there is provided a process for the preparation of 4,4'-bis-(diethylphosphonomethyl)-biphenyl (BPMB), wherein BBMB which is obtained as described above, is further reacted with triethylphosphite (TEP) according to reaction (4), for 0.5 to 1.5 hours at a temperature between 80° C. and 120° C., preferably reflux temperature. The reaction may be carried out with or without a solvent, wherein a preferred solvent is petroleum ether 120–160. The mole ratio between BBMB and TEP is in the range of 1:2 to 1:2.5, preferably 1:2.2. The resulting BPMB is recovered from the reaction mixture, preferably by crystallization.

(4)

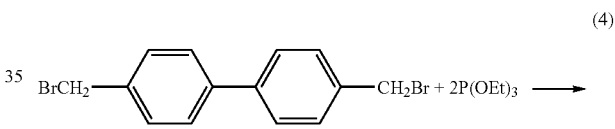

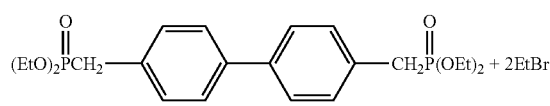

The method of the present invention presents the following advantages:

(1) The bromomethylated compounds obtained via the present process are more reactive than the chloromethylated analogues. Thus facilitating subsequent chemical reactions by requiring more moderate reaction conditions, e.g. lower reaction temperature and shorter reaction time. This is highly beneficial particularly for the reaction with TEP, since lower temperature in said reaction inhibits or prevents TEP decomposition.

(2) Chlorinated bis-methyl ethers which have been known to be halomethylating agents, are highly carcinogenic agents which are forbidden for use in some countries. Hence, BBME provides an alternate less hazardous halomethylating agent.

(3) The use of BBME isolated from stage (a) for the reaction in stage (b) awards better yields and less by-products. Furthermore, said moderate reaction conditions award less Friedel-Crafts reaction by-products and less polymer formation.

EXAMPLES

Example 1

Preparation of bis-bromomethyl ether (BBME)

To a 1 liter reactor equipped with an absorption column with sodium hydroxide 15%, 315 ml HBr (48%) is introduced and 78.8 g paraformaldehyde is added with stirring. Gaseous dry hydrogen bromide is infused to the mixture with cooling of the reactor to a temperature of about 0° C. Paraformaldehyde is dissolved and part of the HBr is absorbed by to the absorption column; The infusing of the hydrogen bromide and stirring are stopped and after 0.5 hours the organic phase (lower layer—containing BBME) is separated from the reaction mass. 97% yield based on paraformaldehyde.

Example 2

Preparation of 4,4'-bis-(bromomethyl)-biphenyl (BBMB)

In a 1 liter reactor equipped with an absorption column with sodium hydroxide 15%, a solution of 265 g BBME, 155.6 g biphenyl in 500 ml dibromomethane and 577 g water solution of zinc bromide (78% w/w) are added. The reaction mass is mixed at 20° C. and simultaneously over 1 hour, 100 g gaseous dry hydrogen bromide is infused to the mixture. After the HBr addition, the reaction mass is stirred intensively for 2 hours at a temperature of about 24° C. to 30° C. The reaction is stopped by adding water (400 ml) to the reaction mass and the stirrer is stopped. The lower organic phase is separated. The organic phase is washed at 40° C. with 400 ml of water during 1 hour and with 100 ml of 5% sodium hydroxide solution and filtered at the same temperature. From the organic solution 150 ml of dibromomethane is distilled and to the residue 350 ml of "Petrol ether 120–140" (PE) is added and the mixture is cooled to 10° C. with stirring. Crystallized BBMB is filtered and washed with 150 ml of PE. 50% yield based on biphenyl.

Example 3

Preparation of 4,4'-bis-(diethylphosphonomethyl)-biphenyl (BPMB)

To BBMB (containing about 156 g of pure compound) obtained according to Example 2, 300 ml of PE is added and after mixing, a suspension of BBMB is transferred to the reactor equipped with two condensers. The first condenser is heated at 60° C. for condensation and recycling to the reactor PE and for removing from the reactor ethyl bromide that is produced in the reaction with triethyl phosphite (TEP). The second condenser is intended for condensation and transfer of ethyl bromide to a collector. To the BBMB suspension in the reactor, 170 g of TEP is added and the mixture is heated under reflux for two hours. After the reaction is over, the solution is cooled to room temperature and BPMB is crystallized. BPMB is filtrated, washed with 200 ml of PE and dried in vacuum at 60° C. The yield is 95% based on BBMB. Purity of BPMB –98%.

While embodiments of the invention have been described by way of illustration, it will be apparent that the invention may be carried out with many modifications, variations and adaptations, without departing from its spirit or exceeding the scope of the claims.

It should be understood that some modification, alteration and substitution is anticipated and expected from those skilled in the art without departing from the teachings of the invention. Accordingly, it is appropriate that the following claims be construed broadly and in a manner consistent with the scope and spirit of the invention

The invention claimed is:

1. A process for bromomethylation of organic compounds, wherein said process is a two stage process comprising of the following steps:
   (a) reacting paraformaldehyde with hydrogen bromide under aqueous conditions for 0.5 to 1.5 hours at a temperature between –0° C. and 20° C., and separating bis-bromomethyl ether (BBME) from the reaction mixture, and,
   (b) reacting BBME obtained in stage (a) with an organic compound selected from the group consisting of substituted or non-substituted phenyl, biphenyl, styryl, naphthyl, pyridyl, thiophene, 5 and 6 member heterocycles, polystyrenes and divinylbenzene-styrene copolymers, in the presence of a Lewis acid selected from the group consisting of zinc bromide, $SnBr_4$ and $AlBr_3$, and under aqueous conditions, to obtain the bromomethylated organic compound.

2. A process according to claim 1 wherein, the HBr used is in gas form.

3. A process for bromomethylation of organic compounds, wherein said process is a two stage process comprising of the following steps:
   (a) reacting paraformaldehyde with hydrogen bromide and separating bis-bromomethyl ether (BBME) from the reaction mixture, and,
   (b) reacting BBME obtained in stage (a) with an organic compound selected from the group consisting of substituted or non-substituted phenyl, biphenyl, styryl, naphthyl, pyridyl, thiophene, 5 and 6 member heterocycles, polystyrenes and divinylbenzene-styrene copolymers, in the presence of a Lewis acid selected from the group consisting of zinc bromide, $SnBr_4$ and $AlBr_3$, to obtain the bromomethylated organic compound wherein, the HBr is introduced to the reaction mixture in the form of an aqueous solution of up to 65% HBr.

4. A process according to claim 3 wherein, the concentration of the aqueous HBr solution is from about 30 weight % to saturation under the reaction conditions.

5. A process according to claim 3 wherein, the HBr aqueous solution is a saturated solution.

6. A process according to claim 1 wherein, the HBr employed is a mixture of HBr gas and an aqueous solution of HBr.

7. A process according to claim 1 wherein, the reaction is carried out at 0° C.

8. A process for bromomethylation of organic compounds, wherein said process is a two stage process comprising of the following steps:
   (a) reacting paraformaldehyde with hydrogen bromide and separating bis-bromomethyl ether (BBME) from the reaction mixture, and,
   (b) reacting BBME obtained in stage (a) with an organic compound selected from the group consisting of substituted or non-substituted phenyl, biphenyl, styryl, naphthyl, pyridyl, thiophene, 5 and 6 member heterocycles, polystyrenes and divinylbenzene-styrene copolymers, in the presence of a Lewis acid selected from the group consisting of zinc bromide, SnBr$_4$ and AlBr$_3$, to obtain the bromomethylated organic compound wherein, stage (a) of the process is carried out as a semi-batch process wherein HBr gas is slowly infused into the reaction medium which contains paraformaldehyde and water.

9. A process according to claim 8 wherein, the reaction mixture further contains an aqueous solution of HBr.

10. A process for bromomethylation of organic compounds, wherein said process is a two stage process comprising of the following steps:
   (a) reacting paraformaldehyde with hydrogen bromide and separating bis-bromomethyl ether (BBME) from the reaction mixture, and,
   (b) reacting BBME obtained in stage (a) with an organic compound selected from the group consisting of substituted or non-substituted phenyl, biphenyl, styryl, naphthyl, pyridyl, thiophene, 5 and 6 member heterocycles, polystyrenes and divinylbenzene-styrene copolymers, in the presence of a Lewis acid selected from the group consisting of zinc bromide, SnBr$_4$ and AlBr$_3$, to obtain the bromomethylated organic compound wherein, stage (a) is carried out in a molar excess of HBr.

11. A process for bromomethylation of organic compounds, wherein said process is a two stage process comprising of the following steps:
   (a) reacting paraformaldehyde with hydrogen bromide and separating bis-bromomethyl ether (BBME) from the reaction mixture, and,
   (b) reacting BBME obtained in stage (a) with an organic compound selected from the group consisting of substituted or non-substituted phenyl, biphenyl, styryl, naphthyl, pyridyl, thiophene, 5 and 6 member heterocycles, polystyrenes and divinylbenzene-styrene copolymers, in the presence of a Lewis acid selected from the group consisting of zinc bromide, SnBr$_4$ and AlBr$_3$, to obtain the bromomethylated organic compound wherein, the mole ratio in stage (b) between BBME and the organic compound is in the range of 1.05:2 to 1.4:2.

12. A process for bromomethylation of organic compounds, wherein said process is a two stage process comprising of the following steps:
   (a) reacting paraformaldehyde with hydrogen bromide and separating bis-bromomethyl ether (BBME) from the reaction mixture, and,
   (b) reacting BBME obtained in stage (a) with an organic compound selected from the group consisting of substituted or non-substituted phenyl, biphenyl, styryl, naphthyl, pyridyl, thiophene, 5 and 6 member heterocycles, polystyrenes and divinylbenzene-styrene copolymers, in the presence of a Lewis acid selected from the group consisting of zinc bromide, SnBr$_4$ and AlBr$_3$, to obtain the bromomethylated organic compound wherein, the mole ratio in stage (b) between the Lewis acid and organic compound is in the range of 1:2 to 1.5:1.

13. A process according to claim 1 wherein, the Lewis acid is zinc bromide.

14. A process for bromomethylation of organic compounds, wherein said process is a two stage process comprising of the following steps:
   (a) reacting paraformaldehyde with hydrogen bromide and separating bis-bromomethyl ether (BBME) from the reaction mixture, and,
   (b) reacting BBME obtained in stage (a) with an organic compound selected from the group consisting of substituted or non-substituted phenyl, biphenyl, styryl, naphthyl, pyridyl, thiophene, 5 and 6 member heterocycles, polystyrenes and divinylbenzene-styrene copolymers, in the presence of a Lewis acid selected from the group consisting of zinc bromide, SnBr$_4$ and AlBr$_3$, to obtain the bromomethylated organic compound wherein, zinc bromide is used in stage (b) in a mole ratio of 1:1 with the organic compound and in the form of a 78% w/w aqueous solution of zinc bromide.

15. A process according to claim 1 wherein the reaction in stage (b) is carried out in an organic solvent selected from among a group comprising of alkanes and brominated alkanes.

16. A process according to claim 15 wherein the solvent is dibromomethane.

17. A process for bromomethylation of organic compounds, wherein said process is a two stage process comprising of the following steps:
   (a) reacting paraformaldehyde with hydrogen bromide and separating bis-bromomethyl ether (BBME) from the reaction mixture, and,
   (b) reacting BBME obtained in stage (a) with an organic compound selected from the group consisting of substituted or non-substituted phenyl, biphenyl, styryl, naphthyl, pyridyl, thiophene, 5 and 6 member heterocycles, polystyrenes and divinylbenzene-styrene copolymers, in the presence of a Lewis acid selected from the group consisting of zinc bromide, SnBr$_4$ and AlBr$_3$, to obtain the bromomethylated organic compound wherein, the reaction in stage (b) is conducted for about 2 to 8 hours at a temperature between 20° C. and 40° C.

18. A process according to claim 17 wherein, the reaction in stage (b) is carried out for about 5 hours at a temperature of about 30° C.

19. A process for bromomethylation of organic compounds, wherein said process is a two stage process comprising of the following steps:
   (a) reacting paraformaldehyde with hydrogen bromide and separating bis-bromomethyl ether (BBME) from the reaction mixture, and,
   (b) reacting BBME obtained in stage (a) with an organic compound selected from the group consisting of substituted or non-substituted phenyl, biphenyl, styryl, naphthyl, pyridyl, thiophene, 5 and 6 member heterocycles, polystyrenes and divinylbenzene-styrene copolymers, in the presence of a Lewis acid selected from the group consisting of zinc bromide, SnBr$_4$ and AlBr$_3$, to obtain the bromomethylated organic compound wherein, the organic compound in stage (b) is biphenyl, the Lewis acid is zinc bromide and the bromomethylated product obtained from stage (b) is 4,4'-bis-(bromomethyl)-biphenyl (BBMB).

20. A process according to claim 19 wherein the mole ratio between zinc bromide and biphenyl is the range of about 1:1 to 3:1.

21. A process according to claim 19 wherein zinc bromide is in the form of a 78% w/w aqueous solution of zinc bromide.

22. A process according to claim 1 wherein, the BBMB obtained is isolated by crystallization.

23. A process for the preparation of 4,4'-bis-(diethylphosphonomethyl)-biphenyl (BPMB) comprising obtaining BBMB according to claim 19 and further reacting said BBMB with triethylphosphite.

24. 4,4'-bis-(bromomethyl)-biphenyl (BBMB) obtained according to a two stage process for bromomethylation of organic compounds, wherein said process is a two stage process comprising of the following steps:
  (a) reacting paraformaldehyde with hydrogen bromide and separating bis-bromomethyl ether (BBME) from the reaction mixture, and,
  (b) reacting BBME obtained in stage (a) with an organic compound selected from the group consisting of substituted or non-substituted phenyl, biphenyl, styryl, naphthyl, pyridyl, thiophene, 5 and 6 member heterocycles, polystyrenes and divinylbenzene-styrene copolymers, in the presence of a Lewis acid selected from the group consisting of zinc bromide, $SnBr_4$ and $AlBr_3$, to obtain the bromomethylated organic compound.

25. 4,4'-bis(diethylphosphonomethyl)-biphenyl (BPMB) whenever obtained according to the process of claim 23.

* * * * *